United States Patent

Müller et al.

[11] Patent Number: 5,773,436
[45] Date of Patent: Jun. 30, 1998

[54] USE OF SEROTONIN ANTAGONISTS FOR TREATING FIBROMYALGIA

[75] Inventors: Wolfgang Müller, Binningen, Switzerland; Thomas Stratz, Bad Säckingen, Germany

[73] Assignee: Novartis AG, Basel, Switzerland

[21] Appl. No.: 721,988

[22] PCT Filed: Apr. 6, 1995

[86] PCT No.: PCT/EP95/01264

§ 371 Date: Dec. 9, 1996

§ 102(e) Date: Dec. 9, 1996

[87] PCT Pub. No.: WO95/27490

PCT Pub. Date: Oct. 19, 1995

[30] Foreign Application Priority Data

Apr. 7, 1994 [GB] United Kingdom .................. 9406857

[51] Int. Cl.⁶ .......................... A61K 31/55; A61K 31/415
[52] U.S. Cl. ............................................. 514/214; 514/397
[58] Field of Search ..................................... 514/214, 397

[56] References Cited

FOREIGN PATENT DOCUMENTS

| | | |
|---|---|---|
| 200444 | 11/1986 | European Pat. Off. . |
| 261964 | 3/1988 | European Pat. Off. . |
| 498466 | 8/1992 | European Pat. Off. . |

OTHER PUBLICATIONS

Zeitschrift für Rheumatologie, vol. 55, No. 6, pp. 335–338 (1994).

Rheumatologia, vol. 32, No. 4, pp. 404–408 (1994).

Br. J. Rheum., vol. 34, No. 3, pp. 283–284 (1995).

*Primary Examiner*—Kimberly Jordan
*Attorney, Agent, or Firm*—Joseph J. Borovian

[57] ABSTRACT

The invention is directed to the use of $5HT_3$ antagonists of formula I

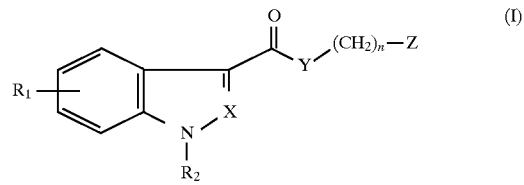

wherein the substituents are as defined herein.

3 Claims, No Drawings

USE OF SEROTONIN ANTAGONISTS FOR TREATING FIBROMYALGIA

This application is a 371 of PCT/EP95/01264, filed Apr. 6, 1995.

This invention relates to a new use of $5HT_3$ antagonists.

These compounds are also referred to hereinafter as compounds of the invention.

$5HT_3$ antagonists are a class of compounds which block $5HT_3$ receptors. Examples include compounds disclosed in Belgian patents 897117, 900425 and 901274. These compounds are described therein as being $5HT_3$ receptor antagonists or serotonin M receptor antagonists (serotonin M receptors have been reclassified as $5HT_3$ receptors).

Other classes of the compounds of the invention are known from e.g. European patent publications 13138A, 200444A, and 214772A and British Patent publication 2153821.

$5HT_3$ antagonists from various sources have been published for a wide variety of uses, for example for the treatment of visceral pain, migraine, vascular and cluster headache, trigeminal neuralgia, arrhythmia, serotonin-induced gastro-intestinal disorders, including emesis induced by anti-cancer agents, anxiety, stress-related psychiatric disorders, depression, cognitive disorders, social withdrawal, panic attacks, agoraphobia, lung embolism, rhinitis or serotonin-induced nasal disorders, for increasing vigilance or for treating dependency induced by dependence-inducing agents. Some have been commercially introduced for the treatment of emesis.

It has now surprisingly been found that the compounds of the invention exert a marked improvement in patients suffering from fibromyalgia, which affects the major symptoms including pain as well as the functional and vegetative disorders and lasts beyond the time of treatment.

Fibromyalgia (also known as fibrositis or generalized tendomyopathy) is a very common disease which is characterized by pains and stiffness in the various regions of the locomotory apparatus, particularly in the region of the tendon insertions and tendon sheaths, which are very sensitive to pressure, furthermore by functional and vegetative disorders as well as psychopathological findings such as depressive conditions and neuroses.

Examples of functional symptoms are sleep disorders, headache, migraine, globus sensation, functional breathing and cardiac complaints, gastrointestinal disorders and dysuria. Examples of vegetative symptoms are cold extremities, hyperhidrosis, dryness of mouth, dermatographia, tremor, respiratory arrhythmia and orthostatic problems.

The treatment of fibromyalgia is very problematic and unsatisfactory. An effective therapy of the disease is not available yet. Attempts to attenuate the pain symptoms using analgesics and non-steroidal anti-inflammatories were unsuccessful. Muscle relaxants showed limited activity at very high dosages which induced considerable side effects and had to be stopped. Antidepressive drugs such as amitriptyline were also proposed and showed some activity in a sub-group of patients, which however decreased rapidly.

The compounds of the invention include compounds of formula I

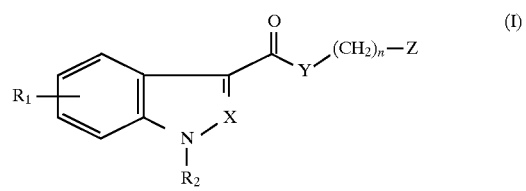

wherein $R_1$ is hydrogen, halogen, hydroxy, alkoxy(1-4C), amino, alkyl(1-4C)amino or dialkyl (1-4C)amino, $R_2$ is hydrogen, alkyl(1-7C), alkenyl(3-6C), alkynyl(3-10C), cycloalkyl(3-7C), cycloalkyl(3-7C)alkyl(1-4C), phenyl, phenylalkyl(1-3C), alkyl(1-6C)carbonyl, alkyl(1-6C) oxycarbonyl, carbamoyl, sulfamoyl or mono- or dialkyl (1-6C)-carbamoyl or -sulfamoyl, X is CH or N and Y is $NR_3$ or O, $R_3$ being hydrogen or alkyl(1-6C), or X+Y together are C-A-N or C-A-CH, wherein A is CH=CH or $-(CH_2)_m-$, m being 2 or 3, n is 0, 1 or 2 and Z is a radical of formula (a)

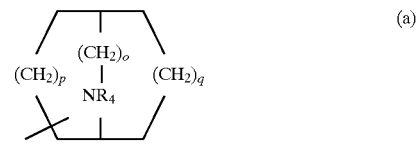

wherein o is 0, p is 0, 1 or 2 and q is 0, 1 or 2, or
o is 1, p is 0 and q is 0 or 1, and
$R_4$ is hydrogen, alkyl(1-7C), cycloalkyl(3-6C), phenylalkyl(1-4C) optionally mono- or disubstituted by halogen, alkyl(1-4C) or alkoxy(1-4C), or a radical of formula (b)

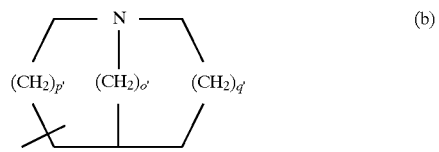

wherein o' is 1, 2 or 3, p' is 0 or 1 and q' is 0 or 1, or a radical of formula (c) or (d)

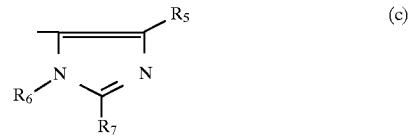

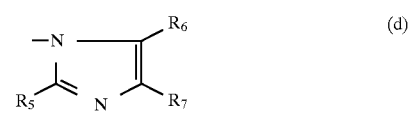

wherein one of $R_5$, $R_6$ and $R_7$ is hydrogen, alkyl(1-6C), cycloalkyl(3-7C), alkenyl(2-6C), phenyl or phenylalkyl(1-3C) and the 2 others independently are hydrogen or alkyl(1-6C), provided that Z is not (d) when n is 0 and Y is $NR_3$ or (with X) N-A-C, in free form or in pharmaceutically acceptable salt or complex form.

$R_1$ is preferably hydrogen or methoxy.

$R_2$ is preferably hydrogen or alkyl(1-7C).

In $R_2$, alkyl(1-7C) is preferably alkyl(1-4C), more preferably methyl, alkenyl(3-6C) is preferably alkenyl(3-4C), alkynyl(3-10C) is preferably alkynyl(3-4C), cycloalkyl(3-7C) is preferably cycloalkyl(3-6C), cycloalkyl(3-7C)alkyl(1-4C) is preferably cycloalkyl(3-6C)methyl, phenylalkyl(1-3C) is preferably benzyl, alkyl(1-6C)carbonyl is preferably alkyl(1-4C)carbonyl, alkyl(1-6C)oxycarbonyl is preferably alkyl(1-4C)oxycarbonyl and dialkyl(1-6C)carbamoyl and -sulfamoyl are preferably dimethylcarbamoyl and -sulfamoyl.

$R_3$ is preferably hydrogen or methyl.

$R_4$ in (a) is preferably hydrogen or alkyl(1-4C), more preferably methyl.

Preferably one of $R_5$, $R_6$ and $R_7$ in (c) and (d) is methyl and the two others are hydrogen. More preferably $R_5$ is methyl and R6 and $R_7$ are hydrogen. When X+Y together are C-$(CH_2)_m$-CH, m is preferably 2.

In (a) preferably o is 0 and p and q are 1 or p is 1 and q is 0.

When Z is of formula (a) or (b), n is preferably 0. When Z is of formula (c) or (d), n is preferably 1.

In a group of compounds of formula I, $R_1$ is alkyl(1-4C), $R_2$ is hydrogen, X is CH, Y is O or NH, n is 0 and Z is of formula (a')

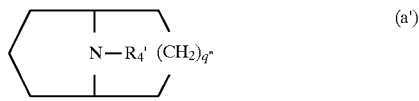

wherein $R'_4$ is methyl, ethyl or propyl and q" is 0, 1 or 2.

Depending on the nature of the substituents defined above, asymmetric carbons may be present in the molecule. This is the case for example when X+Y together are C-A-CH. All optical isomers and their mixtures including the racemic mixtures are part of the present invention.

Furthermore depending on the nature of the Y-$(CH_2)_n$-Z radical, the compounds may present the exo or endo configuration. The exo/endo nomenclature is well known in the literature. Again, both exo and endo forms and their mixtures are part of the present invention.

The endo isomers are preferred.

The compounds of formula I may exist in free form or in salt form. Suitable salt forms include acid addition salts and quaternary ammonium salts.

The compounds of the invention may be chosen from the following compounds:

Indol-3-yl-carboxylic acid-endo-8-methyl-8-aza-bicyclo[3,2,1]-oct-3yl-ester (the hydrochloride is also known as tropisetron, hereinafter compound A);

benzo[b]thiophen-3-yl-carboxylic acid-endo-9-methyl-azabicyclo[3,3,1]) non-3-yl-ester;

5-fluoro-1-methyl-indol-3-yl-carboxylic acid-endo-9-methyl-9-aza-bicyclo[3,3,1]non-3-yl-ester;

1,2,3,9-tetrahydro-9-methyl-3-[(2-methyl-1H-imidazol-1-yl)-methyl]-4H-carbazol-4-one (also known as ondansetron; hereinafter compound B);

1-methyl-indazol-3-yl-carboxylic acid-9-methyl-9-azabicyclo-[3,3,1]non-3α-yl-amide (also known as granisetron);

endo-4-amino-5-chloro-2-methoxy-N-(1-azabicyclo[3,3,1]) non-4-yl)-benzamide;

3-[5-methyl-1H-imidazol-4-yl]-1-(1-methyl-1H-indol-3-yl)-1-propanone;

N-(1-azabicyclo[2,2,2]oct-3-yl)-6-chloro-4-methyl-3-oxo-3,4-dihydro-2H -1,4-benzoxazine-8-carboxamide (also known as azasetron);

N-(endo-8-methyl-8-azabicyclo[3,2,1]oct-3-yl)-2,3-dihydro-2-oxo-1H-benzimidazol-1-carboxamide:

7-methoxy-1H-indol-3-carboxylic acid-(1αH,5αH)-8-methyl-8-aza-bicyclo [3,2,1]oct-3α-yl-ester;

the compound known as GR 87442.

Further preferred 5HT$_3$ antagonists include:

4,5,6,7-tetrahydro-5-[(1-methyl-indol-3-yl)carbonyl] benzimidazole;

(+)-10-methyl-7-(5-methyl-1H-imidazol-4-ylmethyl)-6,7,8,9-tetrahydropy rido[1,2-a]indol-6-one; and N-(1-ethyl-2-imidazolin-2-yl-methyl)-2-methoxy-4-amino-5-chlorobenzamide.

The unexpected efficacy of the compounds of the invention in the treatment of fibromyalgia is established in clinical trials.

In these clinical trials, ambulatory patients suffering from clinically diagnosed fibromyalgia are tested using the 10 cm visual analogue scale for patient self rating (0 =no pain; 10 =severe pain), the "pain score" (pain severity scale) at various body sites and the digital dolorimeter tenderness score at 24 tender points, according to methods described by W. Müller and J. Lautenschläger in Z. Rheumatol 49: 11–21 (1991). A tender point is a localized area of intense pain on deep palpation. Additionally the patients are asked to fill out a form with respect to functional/vegetative symptoms which are evaluated as marked (3), moderate (2), mild (1) or absent (0). These symptoms include:

cold hands or feet dry mouth increased sweating dizziness trembling sleep disturbances gastric disturbances intestinal disturbances, constipation/diarrhea lumpiness in the throat periodic respiratory distress (without previous exertion)

tachycardia/arrhythmia sleepiness, tingling or other abnormal sensations in body parts pain on micturation headache or migraine paresthesia The statistical analysis of the results is effected according to the Wilcoxon test or the Mann-Withney U-test.

In one such trial the compound of the invention was compound A and 17 patients were treated orally during 5 days, with 2×5 mg daily. Eight of those were found to be very good responders (≧40% improvement in the visual analogue score), with the following results:

A significant improvement was observed in the visual analogue scale (p=0.0142), in the pain score (p=0.014), in the dolorimetry (p=0.0208 for the average pressure triggering pain and p=0.0346 for the number of tender points) and in the evaluation of the vegetative symptoms (p=0.0109).

In another trial with compound A, 40 patients were treated. A first group of 20 patients received 2×5 mg daily during 10 days, a second group of 20 patients received 3×5 mg daily during 10 days. Eighteen patients (9 from each group) were found to be very good responders (≧40% improvement in the visual analogue score or in the pain score) with the following results:

A significant improvement was observed in the visual analogue scale (p<0.0003, the score decreasing from 7.6 to 2.6), in the pain score (which decreased from 55.8 to 22.6) and in the dolorimetry (p<0.06 for the average pressure triggering pain, which passed from 1.91 to 2.24 kp, and p<0.02 for the number of tender points which passed from 19.4 to 14.2).

Also the vegetative and functional symptoms improved significantly. For example significative improvements were observed in the symptoms sleep disturbances (p<0.006), cold hands or feet (p<0.002), headaches (p<0.03), paresthesia (p<0.008), tachycardia/arrhythmia (p<0.006) and periodic respiratory distress (p<0.006).

Surprisingly in these trials the achieved improvement of both pain and vegetative symptoms lasted several weeks after therapy.

In still another trial the compound of the invention was compound B and a double-blind study was carried out with 20 patients. The patients received orally 2×8 mg/day of the compound during 5 days and after a pause of 2 days, 2×500 mg/day paracetamol during 5 days (or vice-versa depending on randomization). Eleven patients were found to be very good responders to compound B according to the definition given above, with the following results:

A significant improvement was observed in the visual analogue scale (p=0.003), in the pain score (p=0.022), in the dolorimetry (p=0.008 for the average pressure and p=0.018 for the number of tender points) and in the evaluation of the vegetative symptoms (p=0.003).

Under paracetamol, no significant improvement was observed in the visual analogue scale and in the pain score. In the dolorimeter, the results were significantly negative (decrease of pressure triggering pain, p=0.028; increase of number of tender points, p=0.029).

Again, the good results achieved with compound B lasted several weeks after treatment, during which the general condition of the patients was significantly improved.

These trials are indicative for a long-lasting and disease-modifying (as opposed to merely symptomatic) activity of the compounds.

The compounds of the invention are therefore useful in the treatment of fibromyalgia.

For this indication the appropriate dosage will, of course, vary depending upon, for example, the compound employed, the host, the mode of administration and the nature and severity of the condition being treated. An indicated daily dosage is in the range usually used for known indications such as emesis and is typically from about 0.05 to about 50 mg, conveniently administered, for example, in divided doses up to four times a day, in unit dosage form or in sustained release form.

The compounds of the invention may be administered by any conventional route, in particular enterally, preferably orally e.g. in the form of tablets or capsules, or parenterally, e.g. in the form of injectable solutions or suspensions.

The present invention also provides pharmaceutical compositions comprising the compounds in association with at least one pharmaceutical carrier or diluent for use in the treatment of fibromyalgia. Such compositions may be manufactured in conventional manner. Unit dosage forms may contain for example from about 0.01 mg to about 25 mg of the compound.

The invention further provides the use of a compound of the invention for the manufacture of a pharmaceutical composition for the treatment of fibromyalgia.

The invention futhermore provides a method for the treatment of fibromyalgia in a subject in need of such treatment, which comprises administering to said subject a therapeutically effective amount of a compound of the invention.

We claim:

1. A method for treating fibromyalgia comprising administering to a subject in need of such treatment a therapeutically effective amount of a compound of formula I:

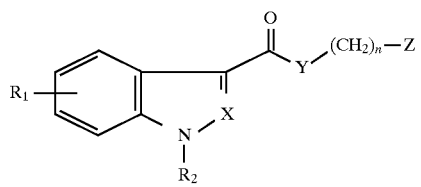

wherein $R_1$ is hydrogen, halogen, hydroxy, alkoxy(1-4C), amino, alkyl(1-4C)amino or dialkyl(1-4C)amino, $R_2$ is hydrogen, alkyl(1-7C), alkenyl(3-6C), alkynyl(3-10C), cycloalkyl(3-7C), cycloalkyl-(3-7C)alkyl(1-4C), phenyl, phenylalkyl(1-3C), alkyl(1-6C)carbonyl, alkyl-(1-6C)oxycarbonyl, carbamoyl, sulfamoyl or mono- or dialkyl (1-6C)carbamoyl or -sulfamoyl, X is CH or N and Y is $NR_3$ or O, $R_3$ being hydrogen or alkyl(1-6C), or X+Y together are C-A-N or C-A-CH, wherein A is CH=CH or $(CH_2)_m$-, m being 2 or 3, n is 0, 1 or 2 and Z is a radical of formula (a)

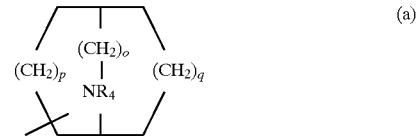

wherein o is 0, p is 0, 1 or 2 and q is 0, 1 or 2, or o is 1, p is 0 and q is 0 or 1, and $R_4$ is hydrogen, alkyl(1-7C), cycloalkyl(3-6C), phenylalkyl(1-4C) optionally mono- or di- substituted by halogen, alkyl(1-4C) or alkoxy(1-4C), or a radical of formula (b)

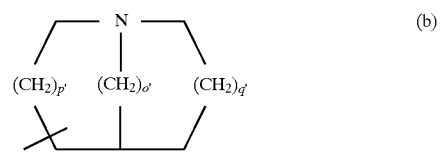

wherein o' is 1, 2 or 3, p' is 0 or 1 and q' is 0 or 1, or a radical of formula (c) or (d)

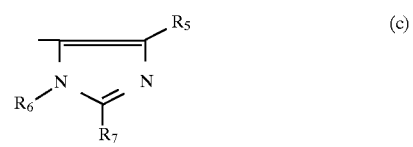

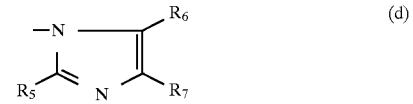

wherein one of $R_5$, R6 and $R_7$ is hydrogen, alkyl(1-6C), cycloalkyl(3-7C), alkenyl(2-6C), phenyl or phenylalkyl(1-3C) and the 2 others independently are hydrogen or alkyl (1-6C), provided that Z is not (d) when n is 0 and Y is $NR_3$ or (with X) N-A-C, in free form or in pharmaceutically acceptable salt or complex form.

2. A method according to claim 1 wherein the 5-$HT_3$ antagonist is indol-3-yl-carboxylic acid-endo-8-methyl-8-aza-bicyclo[3,2,1]-oct-3-yl-ester, in free form or pharmaceutically acceptable salt or complex form.

3. A method according to claim 1 wherein the 5-$HT_3$ antagonist is 1,2,3,9-tetrahydro-9-methyl-[(2-methyl-1H-imidazol-1-yl)-methyl]-4H-carbazol-4-one, in free form or pharmaceutically acceptable salt or complex form.

* * * * *